United States Patent [19]

Boothe et al.

[11] Patent Number: 5,506,631
[45] Date of Patent: Apr. 9, 1996

[54] HORIZONTAL AND VERTICAL GAZE NYSTAGMUS TEST APPARATUS AND METHOD

[76] Inventors: Dennis Boothe, 3175 Ferns Genn Dr., Tallahassee, Fla. 32308; Gary H. Monka, 311 E. 38th St., #4C, New York, N.Y. 10016

[21] Appl. No.: 414,431

[22] Filed: Mar. 31, 1995

[51] Int. Cl.⁶ .................... A61B 3/00; A61B 3/02
[52] U.S. Cl. ............ 351/200; 351/237; 351/246
[58] Field of Search ...................... 351/200, 205, 351/209, 211, 237, 239, 246, 245; 128/745, 733

[56] References Cited

U.S. PATENT DOCUMENTS 3,782,364  1/1974  Watt ............................ 351/200
5,137,345  8/1992  Waldorf et al. ............... 351/206

Primary Examiner—William L. Sikes
Assistant Examiner—Huy Mai
Attorney, Agent, or Firm—Gary H. Monka

[57] ABSTRACT

A Horizontal and Vertical Gaze Nystagmus test apparatus and method for detecting eye twitch of an impaired test subject, the apparatus being generally comprised of a target having a top end for the test subject to focus on and follow with at least one eye through a horizontal range of motion extending between a leftmost location and a rightmost location relative to a central transverse axis, and a through a vertical range of motion, the apparatus further including a base forming a template and support for the target, where the base includes means for positioning thereof relative to the face of the test subject and means for prescribing a uniform travel path for the target between the leftmost and rightmost locations, and the aforementioned vertical range of motion at a specified distance from the face of the test subject.

11 Claims, 3 Drawing Sheets

HORIZONTAL AND VERTICAL GAZE NYSTAGMUS TEST APPARATUS AND METHOD

BACKGROUND

The present invention relates generally to field sobriety testing, and more particularly, to an apparatus and method for administering Horizontal and Vertical Gaze Nystagmus tests to enable an officer of the law to make an initial determination as to the possibility of impairment, and for use as evidence in judicial proceedings.

Driving under the influence of alcohol (D.U.I.) and, to a lesser extent, drugs is responsible for approximately one-half of all motor vehicle fatalities annually in the United States. In recent years, tougher enforcement and penalties have been successful in reducing accidents as a result of drunk driving. Typically, drivers suspected of D.U.I. are stopped and given a battery of field sobriety tests. These include Horizontal Gaze Nystagmus (HGN), Walk and Turn (WAT), One Leg Stand (OLS), Finger-to-Nose (FTN), and Romberg combined with Alphabet Recitation. These are typically administered by the officer to establish probable cause to arrest the suspect on suspicion of DUI. More conclusive evidence of impairment is then established or bolstered through breathalizer and/or blood testing.

"Nystagmus" is defined as an involuntary jerking of the eyeballs. Horizontal Gaze Nystagmus refers to an involuntary jerking of the eyes occurring as the eyes gaze to one side, usually at the point of maximum pupillary deviation. This phenomenon is involuntary and unconscious. The test subject exhibiting the nystagmus is normally unaware of such jerking, and is unable to stop it. When under the influence of alcohol and/or drugs, the jerking of the eyeballs becomes exacerbated and is readily noticeable. Higher concentrations of alcohol and/or drugs result in rapid jerking movement as soon as the pupil moves to the side. Studies have shown that the Horizontal Gaze Nystagmus is the most accurate of the field sobriety tests.

In a typical Horizontal Gaze Nystagmus test, the officer holds an elongated target object such as a pen, pencil or penlight, at a distance of approximately twelve (12) to fifteen (15) inches in front of the suspect. The test subject is then instructed to focus on and track the target as the officer moves it from side to side. An impaired test subject cannot smoothly follow a slow moving object. The average eye tracks approximately 20 degrees per second. When intoxicated, the eyeballs can easily be observed to jerk or bounce as they move horizontally left and right. When the pupil of the eyeball moves to a location of maximum pupillary deviation (the 45 degree position), distinct and aggravated jerking are manifested. Although many people exhibit slight jerking tendencies even when sober, the jerking becomes very pronounced and readily observable when under the influence. The greater the degree of impairment, the sooner the jerking begins. A blood alcohol content (BAC) of 0.10% or more (the legal limit in most states) will likely cause pronounced eyeball jerking well before the eyeball moves to the 45 degree position.

Vertical Gaze Nystagmus testing is used to reveal the possible presence of PCP as well as central nervous system depressants such as alcohol or inhalants. It is most apparent when the test subject has taken high doses of CNS depressants or inhalants. The VGN test is administered in a manner similar to the HGN test, except that in the former the target is moved in a vertical orientation from an initial point at approximately eye of nose level, and the suspect is instructed to track the target until the pupil reaches the 45 degree position.

Recent legal trends have classified field sobriety tests as "testimonial" in nature, i.e., they are subject to the same admissibility conditions and constitutional safeguards as other kinds of testimony in criminal proceedings. Because of these rulings, the Romberg and counting portion of other exercises have been ruled inadmissible unless Miranda warnings were previously read to the suspect. In spite of the fact that HGN has been shown to be a scientifically reliable indicator of alcohol or drug impairment, HGN is often challenged by defense counsel as being unreliable due to the inconsistent administration of the test by police officers in the field. Because the officer performs the test by positioning and then moving the target in front of the test subject without any physical way to control test parameters such as distance and range of motion, the legal attack in court is founded on the premise that since these tests are not uniformly administered, i.e., no control on the foregoing parameters, they are consequently unreliable and therefore should be inadmissable.

SUMMARY OF THE INVENTION

In view of the shortcomings and limitations associated with standard HGN and VGN testing, it is an object of the present invention to provide an apparatus for administering HGN and VGN tests in a uniform manner by incorporating a base and target assembly where the base positions the target at specified distances from the face of the test subject and provides a guide to establish a prescribed path of motion through which the testing officer can move the target to induce involuntary jerking of the eyeballs to ascertain impairment.

It is another object of the present invention to provide an apparatus for performing HGN and VGN tests in a uniform and reliable manner that can be effectively utilized as evidence in DUI proceedings.

It is yet another object of the present invention to provide an apparatus for administering HGN and VGN tests where the apparatus can be easily used with minimum training and maximum effectiveness to determine whether a test subject suspected of operating a motor vehicle under the influence is actually impaired to assist in obtaining probable cause to make an arrest.

It is still another object of the present invention to provide an effective means by which to consistently administer HGN and VGN tests which will hold up as admissible evidence in DUI court proceedings, and ultimately result in a higher DUI conviction rate and safer travel on the roadways for the general public.

It is yet another object of the present invention to provide a method for performing HGN and VGN tests in accordance with the objects enumerated in the foregoing.

In view of the above objects and additional objects which will become apparent hereinafter, the present invention provides a gaze nystagmus test apparatus for detecting eye twitch of an impaired test subject. The apparatus is generally comprised of a target having a top end for the test subject to focus on and follow with at least one eye through a horizontal range of motion extending between a leftmost location on a phantom radial disposed at a first angle relative to a transverse phantom axis disposed through a substantially central location of the face of the test subject during the test and a rightmost location on a phantom radial disposed at a second angle relative to the transverse axis. The apparatus further includes a base forming a template and support for the target, where the base includes means for positioning thereof relative to the face of the test subject and means for prescribing a uniform travel path for the target between the leftmost and rightmost locations at a specified distance from the face of the test subject. The base further includes a handle to facilitate holding, and an integral receptacle or depression which substantially conforms to the area above the lip and under the nose to accurately position the apparatus relative to the face of the test subject consistent with established test parameters.

The apparatus further comprises means for guiding the target member in a vertical range of motion to a maximum elevation at a location disposed on a phantom radial forming a third angle with the transverse axis for the test subject to track the target to a point of maximum pupillary deviation to facilitate VGN testing. During HGN testing, the test subject tracks the target from side to side to respective points of maximum pupillary deviation. During VGN testing, the test subject tracks the target up and down in a similar manner.

The present invention also provides a method for utilizing the apparatus discussed above as will be described below with particular reference to the accompanying drawings.

DETAILED DESCRIPTION OF THE PREFERRED EMBODIMENT

Figure 1:
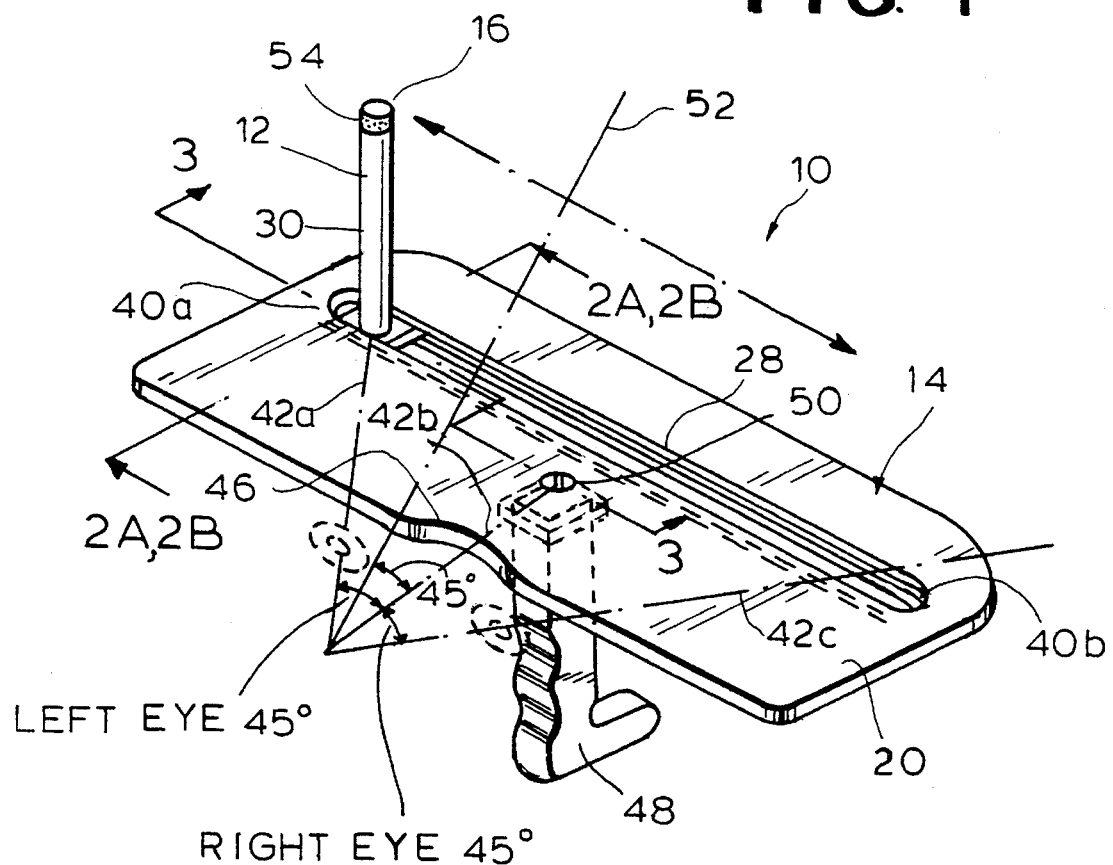
FIG. 1 an isometric view of a first embodiment of an HGN test apparatus in accordance with the present invention.

With reference to the several views of the drawings, there are depicted two exemplary embodiments of an HGN and combination HGN/VGN test apparatus generally denoted by the reference numerals 10a and 10b, respectively.

Figure 2A:
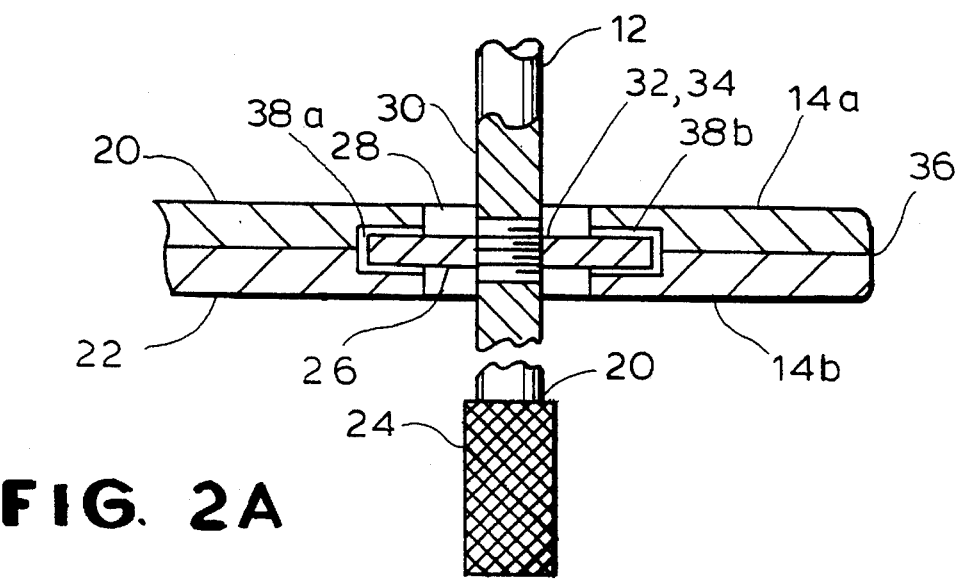
FIG. 2A is a partial sectional view along lines 2A—2A in FIG. 1.

Referring now to FIGS. 1 and 2, the HGN apparatus 10a is principally comprised of a target 12 and base 14. The target 12 and base 14 are preferably constructed from a thermoplastic or like lightweight moldable material, but may be alternatively fabricated from metallic, ceramic or other materials within the scope of the invention. The target 12 is a generally elongated member having a top end 16 disposed to a top side 18 of the base 14, and a bottom end 20 disposed to a bottom side 22 of the base 14 as shown. The target 12 includes a knob or equivalent holding means 24 disposed at bottom end 20 thereof to facilitate grasping and manipulating of the target by the test administrator. Knob 24 may be knurled or provided with surface deformations or undulations for ease of gripping. A sliding retaining member 26 is attached to target 12 to retain the same in a slot 28 formed in the base 12. The retaining member 26 can be bonded to the outer surface 30 of the target 12, or the surface 30 may be provided with male threads 32, and the retaining member 26 provided with corresponding female threads 34 as shown.

The target 12 is of a size typical to that of a pen, pencil or penlight, implements which are all used in prior art HGN and VGN testing.

Figure 2B:
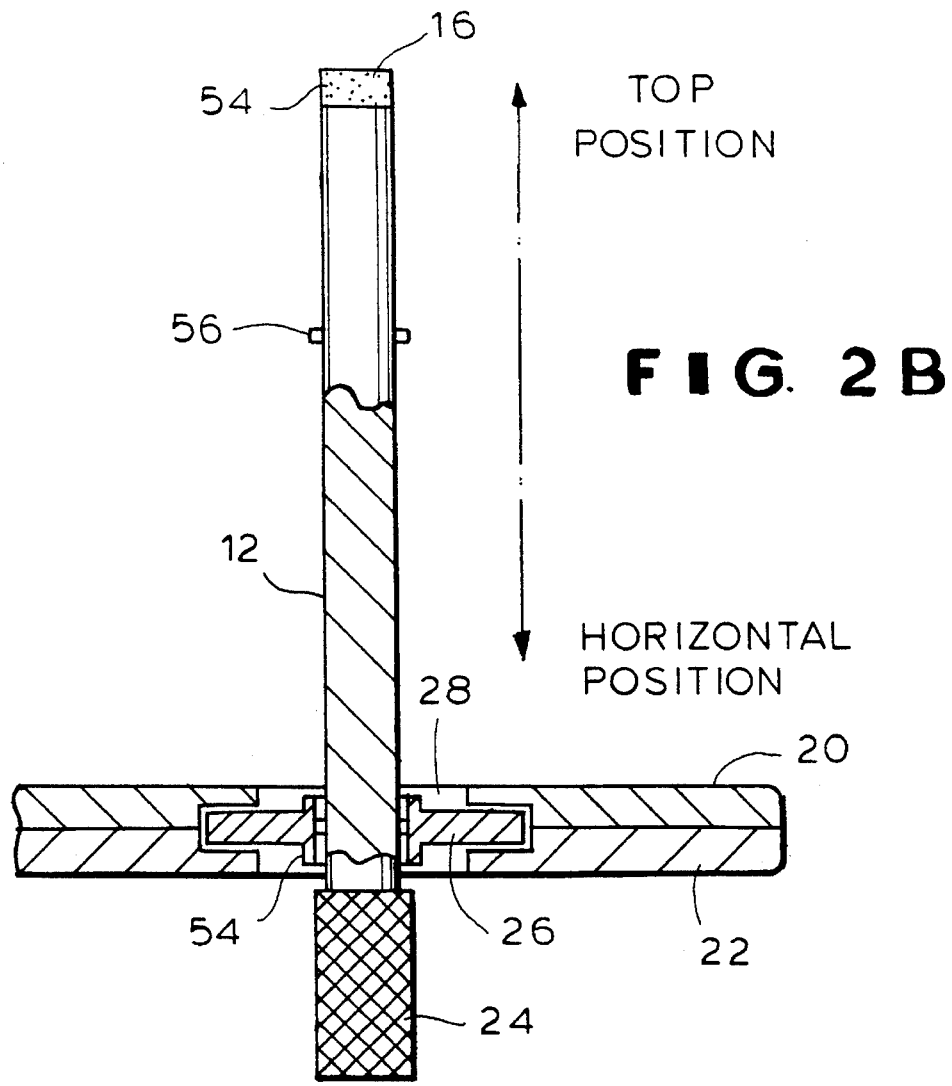
FIG. 2B is a partial sectional view along lines 2B—2B in FIG. 1, showing detail of a modification for administering both HGN and VGN tests.
Figure 3:
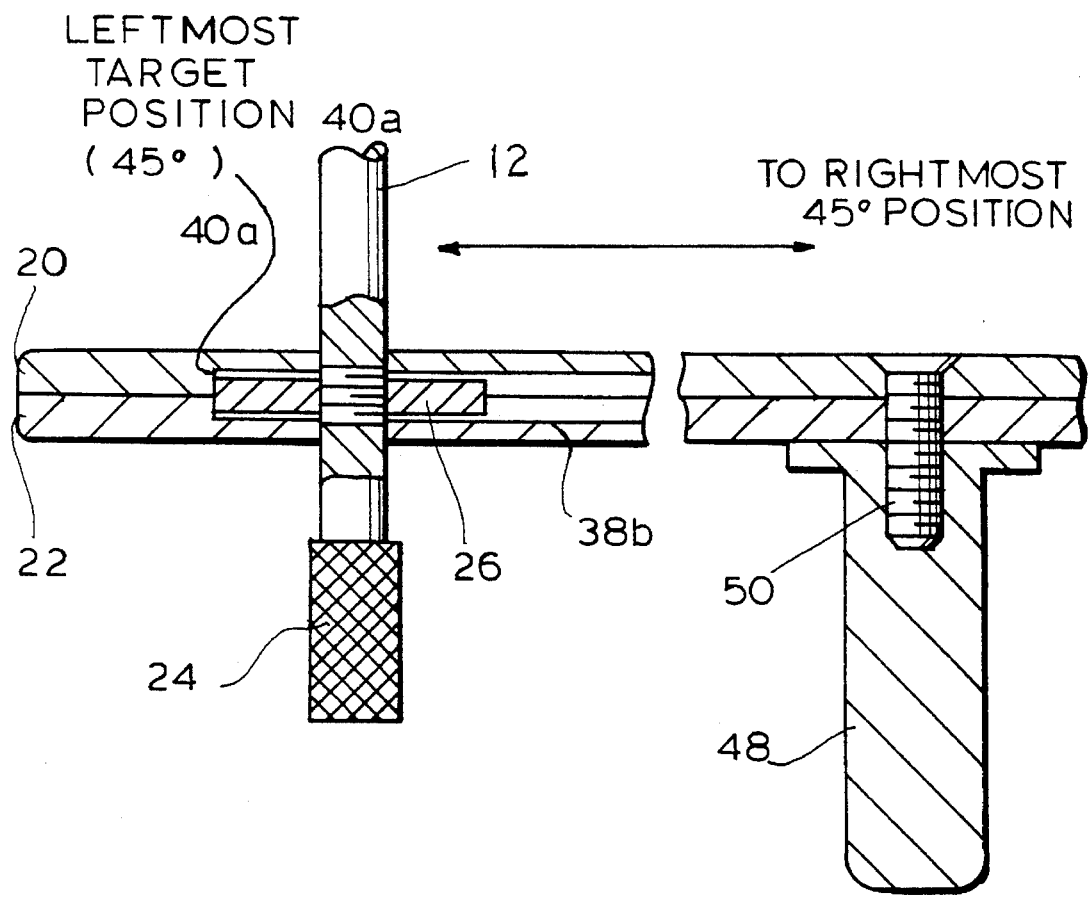
FIG. 3 is a partial sectional view along lines 3—3 in FIG. 1.

As shown in FIGS. 1–3, the base 14 can be constructed as an assembly comprised of a top base half 14a and a bottom base half 14b, which are bonded or otherwise attached along common boundary 36. Slot 28 includes a pair of oppositely disposed and elongated tracks 38a, 38b for slidably receiving retaining member 26. Slot 28 and tracks 38a, 38b extend between a leftmost location 40a and a rightmost location 40b, the respective target travel limits. As shown in FIG. 1, the leftmost location 40a falls on a phantom radial 42a disposed at approximately a 45 degree angle in a counter-clockwise direction when viewed in planform relative to a phantom axis 42b transversely disposed relative to the longitudinal extent of slot 28. Similarly, the leftmost location 40b falls on a phantom radial 42c disposed at approximately a 45 degree angle clockwise relative to transverse axis 42b. The apex 44 where axes 42a, 42b and 42c intersect is located approximately at the nose of the test subject. As discussed above, the travel path of the target 12 should be situated approximately twelve (12) to fifteen (15) inches away from the face. To facilitate and assist in positioning, the base 14 includes an integral depression 46 which fits over and conforms to the area immediately above the lip and below the nose of the test subject. A handle 48 is attached to the bottom 22 of the base 14 with a screw 50 or like attachment means for holding purposes Although shown having an "L-shape," the handle 48 can be made in a variety of configurations and the exemplary embodiment is not intended to be limiting.

Figure 4:
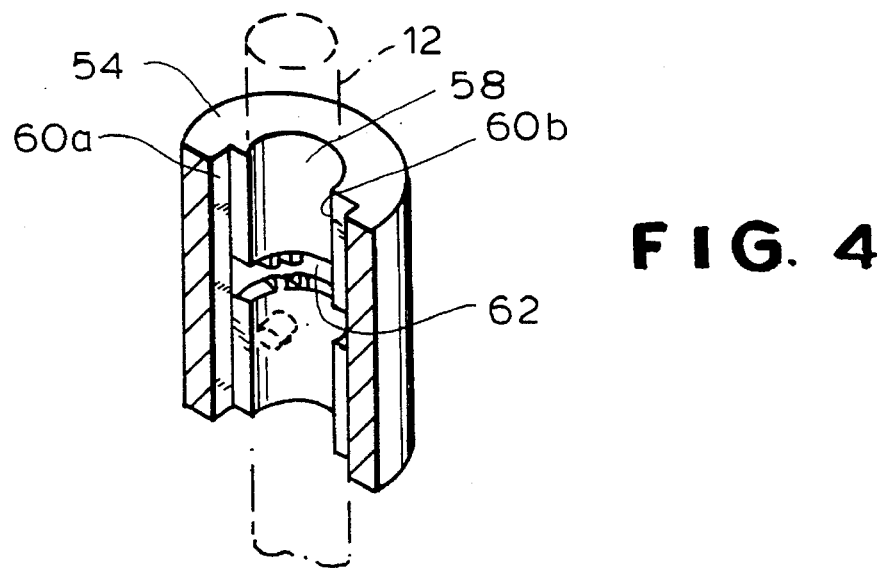
FIG. 4 is an isometric sectional view of the hybrid HGN/VGN modification shown in FIG. 2B.

Referring now to FIGS. 2B and 4, there is depicted an embodiment 10b for administering both HGN and VGN tests. In this connection, the target 12 is provided with a means for locking the same in a fixed vertical position for HGN tests, and for unlocking the target 12 to enable manipulation thereof throughout a vertical range of motion so that the top end 16 is moveable to a maximum elevation 52 located on a phantom radial 42d disposed at approximately a 45 degree angle relative to transverse axis 42b as shown in FIG. 1. To aid in target recognition, the top end 16 thereof may be provided with suitable indicia for the eye to follow. In the exemplary embodiment, the locking means include a collar or sleeve 54 affixed to the sliding member 26 which cooperates with a pair of radially extending retaining pins 56 associated with the target 12. The collar 54 includes a central bore 58 extending therethrough, sized to slidably receive the target 12, a pair of opposed and axially elongated slots 60a, 60b, and at least one annular slot 62. The elevation of target 12 relative to the base 14 can be fixed for administering the HGN test by aligning the retaining pins 56 with annular slot 62 and then rotating the knob 24 to move the pins 56 out of slots 60a, 60b and into slot 62. A plurality of ledges or projections 64 can be incorporated into the upper and lower faces of slot 62 as shown to provide a locking detent to capture retaining pins 56 to fix the target elevation during HGN tests. To release the target 12 for manual manipulation through a vertical range of motion to administer the VGN test, the knob 24 is rotated until the pins 56 become aligned with slots 60a, 60b. The top end 16 of the target 12 can then be repeatedly elevated to point 52 for the eye to track as discussed above.

Prior to performing an HGN test, the officer checks the suspect's eyes to ascertain whether they track together. If one eye lags behind the other, a medical disorder, injury or blindness may be present. Next, the administrator checks to see if both pupils are substantially equal in size. If they are not, the discrepancy might indicate a possible head injury. The eyes are individually checked by having the suspect follow the target to the leftmost and rightmost locations 40*a*, 40*b*. The left eye is checked while the target 12 is moved from the center of the apparatus towards the leftmost location 40*a*, and the right eye is checked while the target 12 moved towards the rightmost location 40*b*. The testing officer looks to determine whether the suspect can smoothly track the target 12. Next, the eyes are checked for distinct jerking at the points of maximum pupillary deviation. The target 12 is moved to the leftmost and rightmost locations 40*a*, 40*b* and the suspect is asked to hold the eye position for about two (2) to three (3) seconds during which the eyes are checked for jerking. After ascertaining whether jerking is exhibited at the points of maximum deviation, the process is repeated, this time with the aim to move the target 12 to the limit over a period of about four (4) seconds, to observe the eyes for the onset of nystagmus. If the test subject's eyes start jerking before they reach the point of maximum pupillary deviation (the 45 degree point), the officer checks to see whether some white of eyeball is visible on the side closest to the respective ear. If no white of the eyeball is observed, either the eye has moved beyond the 45 degree position or the test subject has some abnormality in that the eyes do not track very far to the side. This process is repeated by moving the target 12 through a vertical range of motion to check for VGN. Nystagmus may be triggered by causes other than alcohol, including medications, phencyclidine inhalants, barbiturates and other depressants. A large disparity between the characteristics of the left and right eyes may indicate brain damage. However, intoxication is usually indicated when the eyes cannot follow the target smoothly, when distinct jerking is exhibited when the pupils are at the respective points of maximum pupillary deviation and/or when the onset of jerking occurs prior to reaching the 45 degree position.

The present invention has been shown and described in what are considered to be the most practical and preferred embodiments. The disclosed structure may be altered and it is anticipated that departures may be made therefrom and that obvious modifications will occur to persons skilled in the art.

We claim:

1. A gaze nystagmus test apparatus for detecting eye twitch of an impaired test subject, comprising:

a target for the test subject to focus on and follow with at least one eye through a horizontal range of motion extending between a leftmost location on a phantom radial disposed at a first angle relative to a transverse phantom axis disposed through a substantially central location of the face of the test subject and a rightmost location on a phantom radial disposed at a second angle relative to said transverse axis, said target having a top end; and a base forming a template and support for said target, said base including means for prescribing a uniform travel path for said target between said leftmost and rightmost locations at a specified distance from the face of the test subject for the test subject to track the target from side to side to points of maximum pupillary deviation.

2. The gaze nystagmus test apparatus recited in claim 1, wherein said apparatus further comprises means for guiding said target member in a vertical range of motion to a maximum elevation at a location disposed on a phantom radial forming a third angle with said transverse axis for the test subject to track the target to a point of maximum pupillary deviation.

3. The gaze nystagmus test apparatus recited in claim 2, wherein said first, second and third angles equal approximately 45 degrees.

4. The gaze nystagmus test apparatus recited in claim 1, wherein said base includes means for positioning thereof relative to the face of the test subject to provide a uniform travel path for said target at said specified distance from the face of the test subject.

5. The gaze nystagmus test apparatus recited in claim 1, wherein said base defines a slot forming said prescribed travel path for said target member at said specified distance from the face of the test subject.

6. The gaze nystagmus test apparatus recited in claim 5, wherein said target is operably associated with a means for sliding within said slot.

7. The gaze nystagmus test apparatus recited in claim 5, further comprising means for enabling said target to be freely advanced in a vertical range of motion for the test subject to focus on and follow said top end of said target to an elevation above said base disposed on a phantom radial forming a third angle with said transverse axis, and for fixing an elevated distance of said top end of said target relative to said base.

8. A gaze nystagmus test apparatus for detecting eye twitch of an impaired test subject, comprising:

a target for the test subject to focus on and follow with at least one eye through a horizontal range of motion extending between a leftmost location on a phantom radial disposed at a first angle relative to a transverse phantom axis disposed through a substantially central location of the face of the test subject during the test and a rightmost location on a phantom radial disposed at a second angle relative to said transverse axis, said target having a top end; and a base forming a template and support for said target, said base including means for positioning thereof relative to the face of the test subject and means for prescribing a uniform travel path for said target between said leftmost and rightmost locations at a specified distance from the face of the test subject for the test subject to track the target from side to side to respective points of maximum pupillary deviation.

9. The gaze nystagmus test apparatus recited in claim 8, wherein said apparatus further comprises means for guiding said target member in a vertical range of motion to a maximum elevation at a location disposed on a phantom radial forming a third angle with said transverse axis for the test subject to track the target to a point of maximum pupillary deviation.

10. A gaze nystagmus test method for detecting eye twitch of an impaired test subject, comprising the steps of:

(a) providing a test apparatus having a target for the test subject to focus on and follow with at least one eye through a horizontal range of motion extending between a leftmost location on a phantom radial disposed at a first angle relative to a transverse phantom axis disposed through a substantially central location of the face of the test subject during the test and a rightmost location on a phantom radial disposed at a second angle relative to said transverse axis, said target having a top end; said apparatus further comprising a base forming a template and support for said target, said base including means for positioning thereof relative to the face of the test subject and means for prescribing a uniform travel path for said target between said leftmost and rightmost locations at a specified distance from the face of the test subject for the test subject to track the target from side to side to respective points of maximum pupillary deviation;

(b) moving said target along a uniform travel path between said leftmost and rightmost locations at a specified distance from the face of the test subject for the test subject to track the target through the left eye and right eye, respectively, from side to side to said leftmost and said rightmost locations corresponding to respective points of maximum pupillary deviation; and (c) observing the respective pupils of the test subject at said leftmost and rightmost locations to check for eye twitching indicating possible impairment.

11. The method recited in claim 10, wherein said apparatus further comprises means for guiding said target member in a vertical range of motion where said top end of said target is moved to a maximum elevation disposed on a phantom radial forming a third angle with said transverse axis, and said method further comprises the step of moving said target in a vertical range of motion for the test subject of track the top end of said target to a point of maximum pupillary deviation, and observing the respective pupils of the test subject to check for eye twitching indicating possible impairment.

* * * * *